United States Patent [19]
Stephenson

[11] Patent Number: 5,413,580
[45] Date of Patent: May 9, 1995

[54] CARPAL TUNNEL KNIFE

[76] Inventor: David V. Stephenson, 212 E. 5th St., Valentine, Nebr. 69201

[21] Appl. No.: 219,135

[22] Filed: Mar. 29, 1994

Related U.S. Application Data

[63] Continuation of Ser. No. 77,241, Jun. 14, 1993, abandoned.

[51] Int. Cl.$^6$ ............................................. A61B 17/34
[52] U.S. Cl. .................................. 606/170; 606/167; 606/181; 30/315
[58] Field of Search ............... 606/160, 162, 167, 170, 606/181, 184; 30/167, 280, 305, 294, 314, 315, 340, 343

[56] References Cited

U.S. PATENT DOCUMENTS

| | | | |
|---|---|---|---|
| 40,163 | 10/1863 | Fitch | 30/294 |
| 98,876 | 1/1870 | Merrill | 30/315 |
| 1,095,251 | 5/1914 | Washburne | 30/314 |
| 1,589,683 | 6/1926 | Clinger | 30/315 |
| 2,010,590 | 8/1935 | Grumbacher | 30/315 |
| 2,649,860 | 8/1953 | Royer . | |
| 2,838,049 | 6/1958 | Eisenhofer et al. . | |
| 3,365,798 | 1/1968 | Cunningham | 606/167 |
| 4,365,957 | 12/1982 | Das | 606/160 |
| 4,494,542 | 1/1985 | Lee . | |
| 4,962,770 | 10/1990 | Agee et al. . | |
| 5,064,411 | 12/1991 | Gordon, III | 604/48 |
| 5,119,559 | 6/1992 | Sanabria | 30/315 |
| 5,147,376 | 9/1992 | Pianetti | 606/170 |
| 5,269,796 | 2/1994 | Miller et al. | 606/167 |
| 5,282,816 | 12/1993 | Miller et al. | 606/167 |

FOREIGN PATENT DOCUMENTS

| | | | |
|---|---|---|---|
| 2203341 | 10/1988 | United Kingdom | 606/170 |
| 2206306 | 1/1989 | United Kingdom | 30/340 |

OTHER PUBLICATIONS

The Lawton Company, Surgical Instrument Catalog, pp. 158, 168, 169, 200, New York, N.Y.; 1957.
V. Mueller & Company, *A Comprehensive Guide to Purchasing*, Chicago, Ill., pp. 576, 577, and 601; 1963.

Primary Examiner—Stephen C. Pellegrino
Assistant Examiner—Nancy Mulcare
Attorney, Agent, or Firm—Zarley, McKee, Thomte Voorhees & Sease; Mark D. Frederiksen

[57] ABSTRACT

A surgical knife includes an elongated shaft with a handle mounted on the rearward end of the shaft and oriented perpendicularly thereto. The forward end of the shaft includes a generally planar blade portion which is oriented perpendicularly with respect to the handle. The blade portion includes a pair of forwardly projecting guide fingers separated by a notch, and a cutting edge formed within the notch and extending between the guide fingers.

2 Claims, 1 Drawing Sheet

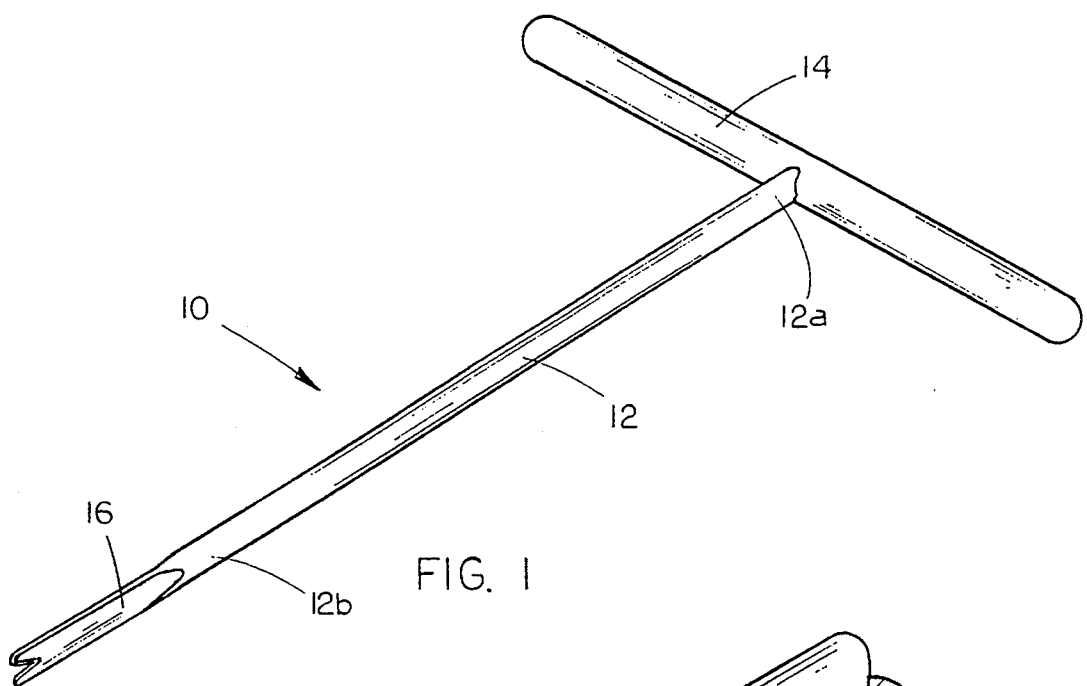
FIG. 1
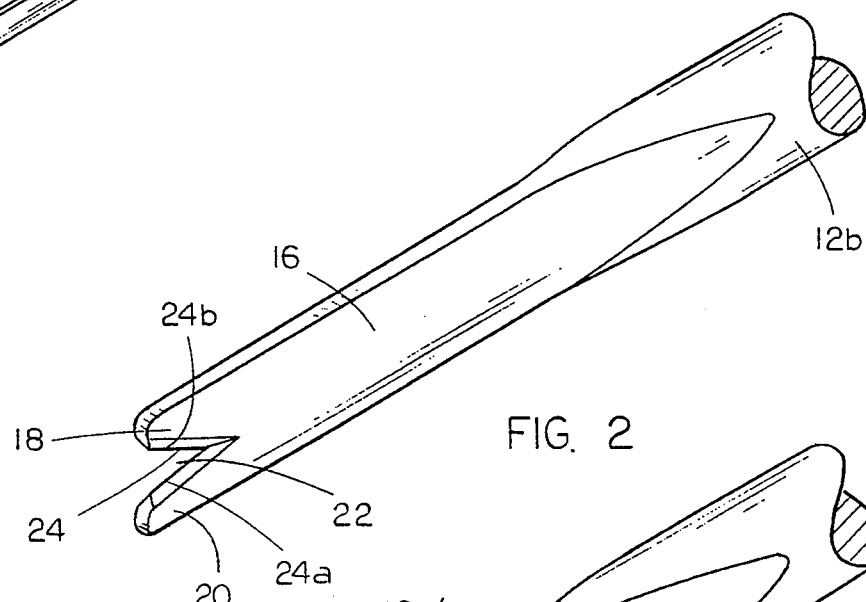
FIG. 2
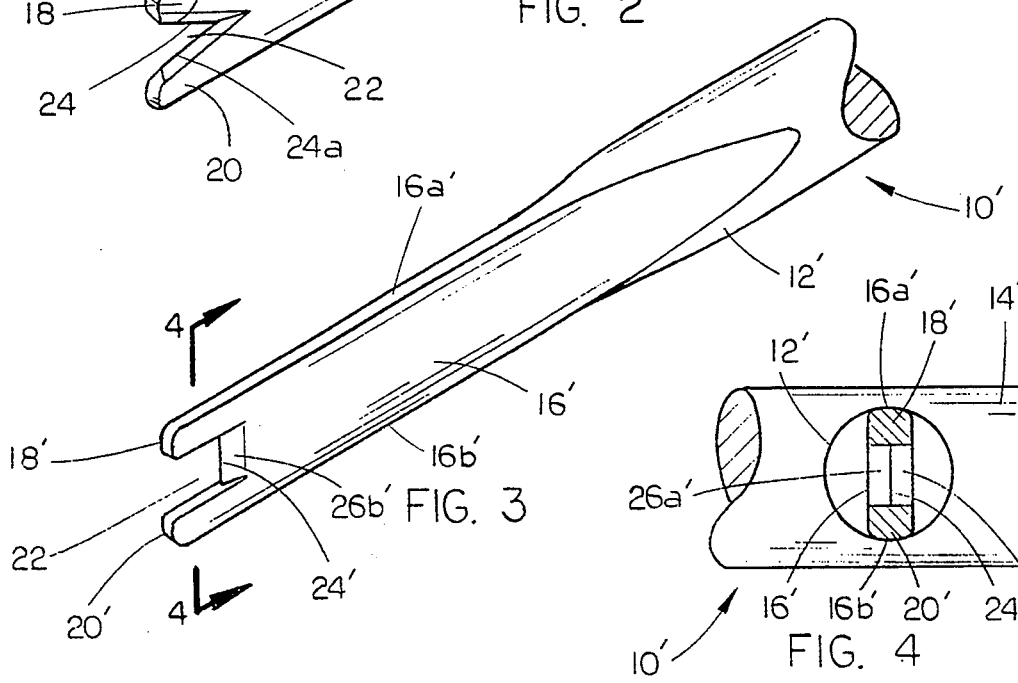
FIG. 3
FIG. 4

CARPAL TUNNEL KNIFE

This is a continuation of Ser. No. 08/077,241, filed Jun. 14, 1993, and now abandoned.

TECHNICAL FIELD

The present invention relates generally to surgical cutting apparatus, and more particularly to an improved knife for division of the transverse carpal ligament.

BACKGROUND OF THE INVENTION

The treatment of carpal tunnel syndrome by releasing the transverse carpal ligament has been utilized for over 50 years. During that time, various methods for releasing the transverse carpal ligament have been developed.

Currently, surgical division of the transverse carpal ligament is initiated by making an incision in the skin on the volar aspect of the wrist at about the level of the distal palmar crease. The fat pad underlying the skin in that area is either retracted or excised to expose the transverse carpal ligament between the lateral edge of the palmaris longus tendon and the hook of the hamate bone. Once the ligament is exposed, a small vertical incision is made in the ligament. A grooved probe is then inserted through the incision in the ligament and advanced into the proximal portion of the palm. The tip of a knife is then placed in the groove of the probe and advanced to divide the ligament. The tissues are retracted and the cut edges of the ligaments are visually examined to assure that the appropriate division has been completed. The probe and knife are then reversed to divide the upper portions of the ligament. Inspection is again conducted to confirm proper division of the ligament.

In the prior art, a conventional knife with a blade along one edge was utilized to perform this surgical procedure. The invasiveness of the procedure required lengthy post-operative recuperation for the hand. Typically, it was necessary to elevate the hand for 24 hours, with the application of ice to the operative site for the first 6-8 hours. Use of the hand was to be avoided for 5-7 days, and active flexion exercises were prescribed 10 times 4 times daily. Preferably, no squeezing or gripping with the hand were to be attempted for a month. In addition, a sling to support the arm for 3-4 weeks was preferred in the prior art.

SUMMARY OF THE INVENTION

It is therefore a general object of the present invention to provide an improved carpal tunnel knife for use in a surgical procedure to divide the transverse carpal ligament.

Another object of the present invention is to provide an improved carpal tunnel knife which reduces wound disruption and post-operative pain.

Yet another other is to provide an improved carpal tunnel knife which reduces post-operative recovery time and restrictions.

These and other objects will be apparent to those skilled in the art.

The surgical knife of the present invention includes an elongated shaft with a handle mounted on the rearward end of the shaft and oriented perpendicularly thereto. The forward end of the shaft includes a generally planar blade portion which is oriented perpendicularly with respect to the handle. The blade portion includes a pair of forwardly projecting guide fingers separated by a notch, and a cutting edge formed within the notch and extending between the guide fingers. In one embodiment of the invention, the cutting edge extends perpendicularly with respect to the upper and lower edges of the cutting fingers. In a second embodiment of the invention the notch is generally V-shaped and the cutting edge is formed along each leg of the V to form a V-shaped cutting edge.

BRIEF DESCRIPTION OF THE DRAWINGS

FIG. 1 is a perspective view of the carpal tunnel knife of the present invention;

FIG. 2 is an enlarged perspective view of the cutting blade of the knife of FIG. 1;

FIG. 3 is an enlarged perspective view of a second embodiment of the cutting blade of the present invention; and FIG. 4 is a sectional view taken at lines 4—4 in FIG. 3.

DESCRIPTION OF THE PREFERRED EMBODIMENTS

Referring now to the drawings, in which similar or corresponding parts are identified with the same reference numeral, and more particularly to FIG. 1, the carpal tunnel knife of the present invention is designated generally at 10 and includes an elongated shaft 12 having a handle 14 mounted to the rearward end 12a of shaft 12.

Preferably, shaft 12 is approximately 7 inches long and 3/16 of an inch in diameter. Handle 14 is preferably formed of an elongated cylindrical member approximately 4 inches long and 5/16 inch in diameter. As shown in FIG. 1, handle fourteen is affixed perpendicular to shaft 12, with shaft 12 generally centered along the length of handle 14.

As shown in FIGS. 1 and 2, the forward end 12b of shaft 12 is flattened to form a generally vertically oriented planar blade 16. Preferably, blade 16 is oriented in a plane perpendicular to the plane defined by shaft 12 and handle 14, as shown in FIG. 1. As shown in FIG. 2, blade 16 includes a forward end 16a having upper and lower spaced-apart guide fingers 18 and 20 respectively. A generally V-shaped notch 22 is formed between fingers 18 and 20 and is defined by a generally V-shaped cutting edge 24. Cutting edge 24 includes a lower cutting edge 24a formed from a pair of beveled walls, and an upper edge 24b also formed from a pair of beveled walls.

Referring now to FIGS. 3 and 4, a second embodiment of the knife is designated generally at 10' and includes the same shaft 12' and handle 14' as described with respect to the first embodiment of FIG. 1. As with the first embodiment, blade 16' is a generally planar member oriented perpendicular to the longitudinal axis of handle 14'.

A pair of guide fingers 18' and 20' project forwardly from the forward end of blade 16' and have a notch 22 formed therebetween. The main difference between the first and second embodiments of the invention lies in the orientation of the cutting edge 24' in the second embodiment of the invention. Rather than having the V-shape of cutting edge 24 of the first embodiment, cutting edge 24' is straight and oriented vertically, perpendicular to the upper and lower edges 16a' and 16b' of blade 16'. As with the first embodiment, cutting edge 24' is formed for a pair of beveled walls 26a and 26b which extend outwardly and rearwardly to form cutting edge 24' at the forward end thereof.

In operation, knife 10 of the present invention is utilized in the same way as prior art knives. Once a small vertical incision has been made in the exposed transverse carpal ligament, a grooved probe in inserted through the incision and the blade 16 of the carpal tunnel knife of the present invention is inserted within the groove. As knife 10 is advanced in the groove of the probe, guide fingers 18 and 20 (and 18' and 20') will quickly and accurately guide the cutting blade 24 or 24' to divide the ligament. The knife 10 of the present invention has been found to nearly eliminate wound disruption, and thereby considerably reduce pain experienced by patients. In addition, post-operative recovery is much shorter. While the preferred embodiment of the invention is manufactured from stainless steel, it is foreseen that a disposable knife could be manufactured from a plastic material with a metal cutting edge.

Whereas the invention has been shown and described in connection with the preferred embodiments thereof, it will be understood that many modifications, substitutions and additions may be made which are within the intended broad scope of the appended claims. There has therefore been shown and described an improved carpal tunnel knife which accomplishes at least all of the above stated objects.

I claim:

1. A surgical knife for dividing the transverse carpal ligament, comprising:
   an elongated shaft having forward and rearward ends;
   a handle having a longitudinal axis and mounted perpendicularly to the shaft on the rearward end of said shaft;
   said forward end of said shaft having a generally planar blade portion oriented perpendicularly with respect to the longitudinal axis of said handle;
   said blade portion having a cutting edge formed in a forward end thereof, for cutting said transverse carpal ligament;
   said forward end of said blade portion including a pair of forwardly projecting guide fingers separated by a notch extending rearwardly into the forward end of said blade portion, said cutting edge formed within said notch so as to extend between said guide fingers; and
   said notch being generally V-shaped with each leg of the "V" having a cutting edge formed therealong, to thereby form a V-shaped cutting edge.

2. A surgical knife for dividing the transverse carpal ligament, comprising:
   an elongated shaft having forward and rearward ends;
   a handle having a longitudinal axis and mounted perpendicularly to the shaft on the rearward end of said shaft;
   said forward end of said shaft having a generally planar blade portion oriented perpendicularly with respect to the longitudinal axis of said handle;
   said blade portion having a cutting edge formed in a forward end thereof, for cutting said transverse carpal ligament;
   said forward end of said blade portion including a pair of forwardly projecting guide fingers separated by a notch extending rearwardly into the forward end of said blade portion, said cutting edge formed within said notch so as to extend between said guide fingers; and
   said notch being generally V-shaped with at least one leg of the "V" having a cutting edge formed therealong.

* * * * *